United States Patent
Peltz et al.

(10) Patent No.: US 6,294,347 B1
(45) Date of Patent: Sep. 25, 2001

(54) HUMAN FCγ RECEPTOR III

(75) Inventors: Gary A. Peltz, Redwood City; Kevin W. Moore, Palo Alto, both of CA (US)

(73) Assignee: Applied Research Systems ARS Holding N.V., Curacao (AN)

( * ) Notice: Subject to any disclaimer, the term of this patent is extended or adjusted under 35 U.S.C. 154(b) by 0 days.

(21) Appl. No.: 09/232,218

(22) Filed: Jan. 19, 1999

Related U.S. Application Data (62) Division of application No. 08/417,488, filed on Apr. 5, 1995, now Pat. No. 5,976,831, which is a continuation of application No. 08/218,985, filed on Mar. 29, 1994, now abandoned, which is a continuation of application No. 08/089,907, filed on Jul. 9, 1993, now abandoned, which is a continuation of application No. 07/956,814, filed on Oct. 5, 1992, now abandoned, which is a continuation of application No. 07/603,736, filed as application No. PCT/US89/02182 on May 24, 1989, which is a continuation of application No. 07/300,039, filed on Jan. 19, 1989, now abandoned, which is a continuation-in-part of application No. 07/199,513, filed on May 27, 1988, now abandoned.

(51) Int. Cl.[7] .................................................. G01N 33/567
(52) U.S. Cl. ........................... 435/7.21; 435/7.1; 435/7.2; 435/356; 435/365; 530/350; 436/501; 436/503; 436/504; 436/536; 436/542
(58) Field of Search ..................................... 436/501, 503, 436/504, 536, 542; 435/7.1, 7.2, 69.1, 7.21, 325, 320.1, 356, 365, 70.1, 70.3; 530/350

(56) References Cited

U.S. PATENT DOCUMENTS 5,219,728   6/1993   Khayat .

FOREIGN PATENT DOCUMENTS

| 0 330 191 | 8/1989 | (EP) . |
| 87/07277 | 12/1987 | (WO) . |
| 89-11490 | 11/1989 | (WO) . |

OTHER PUBLICATIONS

Simmons et al., Nature 333:568–570.*
Lewis et al., Nature 324:372–375.*
Fleit et al., The Journal of Immunology 140(9):3120–25.*
Unkeless et al., Ann.Rev.Immunol. 6:251–81.*
Anderson et al, "Human Leukocyte IgG Fc receptors", *Immunology Today* 7(9):264–266 (1986).
Anderson et al, "Structural Polymorphism of the Human Monocyte 40 kilodalton Fc Receptor for IgG", *J. Immunol.* 138:2254–2256 (1987).
Aruffo et al, "Molecular cloning of a CD28 cDNA by a high–efficiency COS cell expression system", *Proc. Natl. Acad. Sci. USA* 84:8573–8577 (1987).
Clarkson et al, "Treatment of Refractory Immune Thrombocytopenic Purpura with an Anti–Fcgamma–Receptor Antibody", *NE J. Med.* 314(19):1236–1239 (1985).
Fleit et al, "Human neutrophil Fcgamma receptor distribution and structure", *Proc. Natl. Acad. Sci. USA* 79:3275–3279 (1982).
Fleit et al, "Biochemical Characterization of an Fcgamma Receptor Purified from Human Neutrophils", *J. Immunol.* 140(9):3120–3125 (May 1988).
Graziano et al, "FcgammaRI and FcgammaRII on Monocytes and Granulocytes Are Cytotoxic Trigger Molecules for Tumor Cells", *J. Immunol.* 139(10):3536–3541 (1987).
Hibbs et al, "Molecular cloning of a human immunoglobulin G Fc receptor", *Proc. Natl. Acad. Sci. USA* 85:2240–2244 (1988).
Khayat et al, "Soluble circulating Fcgamma receptors in human serum: A new ELISA assay for specific and quantitative detection", *J. Immunol. Methods* 100:235–241 (1987).
Kurlander et al, "The Blockade of Fc Receptor–Mediated Clearance of Immune Complexes in vivo by a Monoclonal antibody (2.4G2) Directed against Fc Receptors on Murine Leukocytes", *J. Immunol.* 133 (2):885–862 (1984).
Lanier et al, "Co–association of CD3's with a receptor (CD16) for IgG Fc on human natural killer cells", *Nature* 342:803–807 (1989).
Lewis et al, "A complementary DNA clone for a macrophage–lymphocyte Fc receptor", *Nature* 324:372–375 (Nov. 1986).
Perussia et al, "The Fc Receptor for IgG on Human Natural Killer Cells: Phenotypic, Functional, and Comparative Studies with Monoclonal Antibodies", *J. Immunol.* 133(1):180–89 (1984).
Shen et al, "Polymorphonuclear Leukocyte Function Triggered through the High Affinity Fc Receptor for Monomeric IgG", *J. Immunol.* 139(2):534–538 (1987).
Simmons et al, "The Fcgamma receptor of natural killer cells is a phospholipid–linked membrane protein", *Nature* 333:568–570 (Jun. 1988).
Unkeless et al, "Structure and Function of Human and Murine Receptors for IgG", *Ann. Rev. Immunol.* 6:251–280 (1988).
Vaughn et al, "Characterization of Human IgG Fc Receptors", *J. Immunol.* 135(6):4059–4065 (1985).
Young et al, "Efficient isolation of genes by using antibody probes", *Proc. Natl. Acad. Sci. USA* 80:1194–1198 (1983).

* cited by examiner

*Primary Examiner*—Lorraine Spector
*Assistant Examiner*—Eliane Lazar-Wesley
(74) *Attorney, Agent, or Firm*—Browdy and Neimark (57) ABSTRACT

Soluble and membrane-bound forms of human FcγRIII are provided, together with nucleic acids capable of encoding the same. Soluble FcγRIIIs are useful in ameliorating the serum platelet deficiency associated with immune thrombocytopenic prupura. Cells expressing membrane-bound FcγRIIIs are useful components in assays for serum immune complexes.

2 Claims, 5 Drawing Sheets

FIG. 1A

```
         10                    30                    50
CACTCCAGTGTGGCATCATGTGGCAGCTGCTCCTCCCAACTGCTCTGCTACTT
                 MetTrpGlnLeuLeuLeuProThrAlaLeuLeuLeu
         110                   130                   150.
GTTCCTGGAGCCTCAATGGTACAGGGTGCTCGAGAAGGACAGTGTGACTCTG
lPheLeuGluProGlnTrpTyrArgValLeuGluLysAspSerValThrLeu
         210                   230                   250
CACAATGAGAACCTCATCTCAAGCCAGGCCTCGAGCTACTTCATTGACGCTGCC
HisAsnGluAsnLeuIleSerSerGlnAlaSerSerTyrPheIleAspAlaAla
         310                   330                   350
CCCTCAGTGACCCGGTGCAGCTAGAAGTCCATGTCGGCTGGCTGTTGCTCCAG
hrLeuSerAspProValGlnLeuGluValHisValGlyTrpLeuLeuLeuGln
         410                   430                   450
TCACAGCTGGAAGAACACTGCTCTGCATAAGGTCACATATTTACAGAATGGC
sHisSerTrpLysAsnThrAlaLeuHisLysValThrTyrLeuGlnAsnGly
         510                   530                   550
GCCACACTCAAAGATAGCGGCTCCTACTTCTGCAGGGGGCTTGTTGGGAGTAAA
AlaThrLeuLysAspSerGlySerTyrPheCysArgGlyLeuValGlySerLys
         610                   630                   650
CAGTGTCAACCATCTCATCATTCTCTCCACCTGGGTACCAAGTCTCTTTCTGC
laValSerThrIleSerSerPheSerProProGlyTyrGlnValSerPheCys
         710                   730                   750
TGTGAAGACAAACATTTGAAGCTCAACAAGAGACTGGAAGGACCATAAACTTA
rValLysThrAsnIleEnd
```

```
AATAAGAGCAGTGGCAGCAGCATCTCTGAACATTTCTCTGGATTTGCAACCCC
GCCAGATCCTTTATCCAACTCTCGATTTTTCCTTGGTCTCCAGTGGAAGGGAA
CTAGAAATTGAAGTTTCAGAGCTACACAAACACTTTTTCTGTCCCAACCATTC
CATACAAAAATTGCTCGTATTATAAATTACCCAGTTTAGAGGGGAAAAAAGAA
AGGACCCTACAGAGTGTGGGAACTGCTGGGGATCTAGAGAATTCAGTGGGACC
GGGAGGTGTTCCCATCTGAGCCCAGAGATAAGGGTGTCTTCCTAGAACATTAG
CTTCCAGGGGACTCTATCAGAACTGGACCATTTCCAAGTATATAACGATGAGC
TTGGGGTGGGGGTGGGGTGGAAAAGAAAGTACAGAACAAACCCTGTGTCACTG
AATGAGAAAGCCTGAGAAGAAAGAACCAACCACAAGCACACAGGAAGGAAAGC
TTAATGCAGGGACTGTAAAACCACCTTTTCTGCTTCAATGTCTAGTTCCTGTA
TAAATGTACTACTGAGCTTCACTGAGTTACGCTGTGAAACTTTCAAATCCTTC
ATGAAAAAAGCTTTAGCTGTCTCCTGTTTTGTAAGCTTTCAGTGCAACATTT
```

FIG. 1B

```
              70    +1                       90
      CTAGTTTCAGCTGGCATGCGGACTGAAGATCTCCCAAAGGCTGTGGT
      LeuValSerAlaGlyMetArgThrGluAspLeuProLysAlaValVa
              170                           190
      AAGTGCCAGGGAGCCTACTCCCCTGAGGACAATTCCACACAGTGGTTT
      LysCysGlnGlyAlaTyrSerProGluAspAsnSerThrGlnTrpPhe
              270                           290
       ACAGTCGACGACAGTGGAGAGTACAGGTGCCAGACAAACCTCTCCA
       ThrValAspAspSerGlyGluTyrArgCysGlnThrAsnLeuSerT
              370                           390
      GCCCCTCGGTGGGTGTTCAAGGAGGAAGACCCTATTCACCTGAGGTG
      AlaProArgTrpValPheLysGluGluAspProIleHisLeuArgCy
              470                           490
      AAAGACAGGAAGTATTTTCATCATAATTCTGACTTCCACATTCCAAAA
      LysAspArgLysTyrPheHisHisAsnSerAspPheHisIleProLys
              570                           590
        AATGTGTCTTCAGAGACTGTGAACATCACCATCACTCAAGGTTTGG
        AsnValSerSerGluThrValAsnIleThrIleThrGlnGlyLeuA
              670                           690
       TTGGTGATGGTACTCCTTTTTGCAGTGGACACAGGACTATATTTCTC
       LeuValMetValLeuLeuPheAlaValAspThrGlyLeuTyrPheSe
              770                           790
      AATGGAGAAAGGACCCTCAAGACAAATGACCCCCATCCCATGGGAGT
```

| | |
|---|---|
| ATCATCCTCAGGCCTCTCTACAAGCAGCAGGAAACATAGAACTCAGA | |
| AAGCCCATGATCTTCAAGCAGGGAAGCCCCAGTGAGTAGCTGCATTC | 1000 |
| CCTCACAGTAAAACAACAATACAGGCTAGGGATGGTAATCCTTTAAA | |
| AATAATTATTCCTAAACAAATGGATAAGTAGAATTAATGATTGAGGC | 1200 |
| AATGAAAGCATGGCTGAGAAATAGCAGGGTAGTCCAGGATAGTCTAA | |
| CCGTAGTGGAATTAACAGGAAATCATGAGGGTGACGTAGAATTGAGT | 1400 |
| CCTCTAATGCTAGGAGTAGCAAATGGTCCTAGGAAGGGACTGAGGA | |
| TCCCAAGTTAAGCTAAGTGAACAGAACTATCTCAGCATCAGAATGAG | 1600 |
| GCAGGAGGTGAAAATGCTTTCTTGGCCAGGGTAGTAAGAATTAGAGG | |
| TAGCTTTGTTCATTGCATTTATTAAACAAATGTTGTATAACCAATAC | 1800 |
| TTCAGTCAGTTCCAATGAGGTGGGGATGGAGAAGACAATTGTTGCTT | |
| CTTGGTTCCAATAAAGCATTTTACA (A)n | 2000 |

```
         10                  30                  50
GGGGGGGGGGGGGGGTAAATCCGCAGGACCTGGGTAACACGAGGAAGGGCTCCG
         110                 130                 150
TGCTCCTCCCAACTGCTCTGCTACTTCTAGTTTCAGCTGGCATGCGGACTGAA
euLeuLeuProThrAlaLeuLeuLeuLeuValSerAlaGlyMetArgThrGlu
         210                 230                 250
GCTCGAGAAGGACAGTGTGACTCTGAAGTGCCAGGGAGCCTACTCCCCTGAG
lLeuGluLysAspSerValThrLeuLysCysGlnGlyAlaTyrSerProGlu
         310                 330                 350
GCCTCGAGCTACTTCATTGACGCTGCCACAGTCGACGACAGTGGAGAGTACAGG
AlaSerSerTyrPheIleAspAlaAlaThrValAspAspSerGlyGluTyrArg
         410                 430                 450
TCCATATCGGCTGGCTGTTGCTCCAGGCCCCTCGGTGGGTGTTCAAGGAGGAA
alHisIleGlyTrpLeuLeuLeuGlnAlaProArgTrpValPheLysGluGlu
         510                 530                 550
TAAGGTCACATATTTACAGAATGGCAAAGGCAGGAAGTATTTTCATCATAAT
sLysValThrTyrLeuGlnAsnGlyLysGlyArgLysTyrPheHisHisAsn
         610                 630                 650
TTCTGCAGGGGGCTTTTTGGGAGTAAAAATGTGTCTTCAGAGACTGTGAACATC
PheCysArgGlyLeuPheGlySerLysAsnValSerSerGluThrValAsnIle
         710                 730                 750
CACCTGGGTACCAAGTCTCTTTCTGCTTGGTGATGGTACTCCTTTTTGCAGTG
roProGlyTyrGlnValSerPheCysLeuValMetValLeuLeuPheAlaVal
         810                 830                 850
AAGAGACTGGAAGGACCATAAATTTAAATGGAGAAAGGACCCTCAAGACAAATGA
rArgAspTrpLysAspHisLysPheLysTrpArgLysAspProGlnAspLysEnd

GAACATTTCTCTGGATTTGCAACCCCATCATCCTCAGGCCTCTCTACAAGCAGCA
TTTCCTTGGTCTCCAGTGGAAGGGAAAAGCCCATGATCTTCAAGCAGGGAAGCCC
AAACACTTTTTCTGTCCCAACCGTTCCCTCACAGCAAAGCAACAATACAGGCTAG
TACCCAGTTTAGAGGGGAAAAAAAAACAATTATTCCTAAATAAATGGATAAGTAG
GGGATCTAGGGAATTCAGTGGGACCAATGAAAGCATGGCTGAGAAATAGCAGGTA
AAGGGTGTCTTCCTAGAACATTAGCCGTAGTGGAATTAACAGGAAATCATGAGGG
ATCTCCAAGTATATAACGATGAGTCCTCTTAATGCTAGGAGTAGAAAATGGTCCT
AGTACAGAACAAACCCTGTGTCACTGTCCCAAGTTGCTAAGTGAACAGAACTATC
GCACACAGGAAGGGGGCGCAGGAGGTGAAAATGCTTTCTTGGCCAGGGTAGTAA
CAATATCTAATTCCTGTGTAGCTTTGTTCATTGCATTTATTAAACAAATGTTGTA
GAAACTTTCAAATCCTTCATCATGTCAGTTCCAATGAGGTGGGGATGGAGAAGAC
GCTTTAAGCGCAACATTTCTTGGTTCCAATAAAGCATTTTACAAGATCTTGCATG
ATGATAAAAAAAAAAAAAAAAAAAA
```

```
                70                          90
GATATCTTTGGTGACTTGTCCACTCCAGTGTGGCATCATGTGGCAGC
                                         MetTrpGlnL
               170                         190
GATCTCCCAAAGGCTGTGGTGTTCCTGGAGCCTCAATGGTACAGGGT
AspLeuProLysAlaValValPheLeuGluProGlnTrpTyrArgVa
               270                         290
GACAATTCCACACAGTGGTTTCACAATGAGAGCCTCATCTCAAGCCAG
AspAsnSerThrGlnTrpPheHisAsnGluSerLeuIleSerSerGln
               370                         390
  TGCCAGACAAACCTCTCCACCCTCAGTGACCCGGTGCAGCTAGAAG
  CysGlnThrAsnLeuSerThrLeuSerAspProValGlnLeuGluV
               470                         490
GACCCTATTCACCTGAGGTGTCACAGCTGGAAGAACACTGCTCTGCA
AspProIleHisLeuArgCysHisSerTrpLysAsnThrAlaLeuHi
               570                         590
TCTGACTTCTACATTCCAAAAGCCACACTCAAAGACAGCGGCTCCTAC
SerAspPheTyrIleProLysAlaThrLeuLysAspSerGlySerTyr
               670                         690
 ACCATCACTCAAGGTTTGGCAGTGTCAACCATCTCATCATTCTTTC
 ThrIleThrGlnGlyLeuAlaValSerThrIleSerSerPhePheP
               770                         790
 GACACAGGACTATATTTCTCTGTGAAGACAAACATTCGAAGCTCAAC
 AspThrGlyLeuTyrPheSerValLysThrAsnIleArgSerSerTh
               870                         890
    CCCCCATCCCATGGGGGTAATAAGAGCAGTAGCAGCAGCATCTCT
```

| | |
|---|---|
| GGAAACATAGAACTCAGAGCCAGATCCCTTATCCAACTCTCGACT | 1000 |
| CAGTGAGTAGCTGCATTCCTAGAAATTGAAGTTTCAGAGCTACAC | |
| GGATGGTAATCCTTTAAACATACAAAAATTGCTCGTGTTATAAAT | 1200 |
| AATTAATGGTTGAGGCcAGGACCATACAGAGTGTGGGAACTGCTG | |
| GTCCAGGATAGTCTAAGGGAGGTGTTCCCATCTGAGCCCAGAGAT | 1400 |
| TGACGTAGAATTGAGTCTTCCAGGGGACTCTATCAGAACTGGACC | |
| AGGAAGGGGACTGAGGATTGCGGTGGGGGTGGGGTGGAAAAGAA | 1600 |
| TCAGCATCAGAATGAGAAAGCCTGAGAAGAAAGAACCAACCACAA | |
| GAATTAGAGGTTAATGCAGGGACTGTAAAACCACCTTTTCTGCTT | 1800 |
| TAACCAATACTAAATGTACTACTGAGCTTCGCTGAGTTAAGTTAT | |
| AATTGTTGCTTATGAAAGAAAGCTTTACGTGTCTCTGTTTTGTAA | 2000 |
| CTACTCTTAGATAGAAGATGGGAAAACCATGGTAATAAAATATGA | |
| | 2200 |

HUMAN FCγ RECEPTOR III

CROSS-REFERENCE TO RELATED APPLICATIONS

The present application is a division of U.S application Ser. No. 08/417,488, filed Apr. 5, 1995, now U.S. Pat. No. 5,976,831 which is a continuation of U.S. application Ser. No. 08/218,985, filed Mar. 29, 1994, now abandoned, which is a continuation of U.S. application Ser. No. 08/089,907, filed Jul. 9, 1993, now abandoned, which is a continuation of U.S. application Ser. No. 07/956,814, filed Oct. 5, 1992, now abandoned, which is a continuation of U.S. application Ser. No. 07/603,736, filed Nov. 15, 1990, now abandoned, which is the United States national §371 application corresponding to International Application Ser. No. PCT/US89/02182, filed May 24, 1989, and designating the United States, which PCT application is, in turn, a continuation of U.S. application Ser. No. 07/300,039, filed Jan. 19, 1989, now abandoned, which is a continuation-in-part of U.S. application Ser. No. 07/199,513, filed May 27, 1988, now abandoned.

FIELD OF THE INVENTION

The invention relates generally to therapeutic compounds, and more particularly to soluble and membrane-bound forms of a low-affinity receptor for human immunoglobulin G, nucleic acids encoding the same, and diagnostic and therapeutic uses of such receptors.

BACKGROUND

Receptors for the Fc portion of immunoglobulin G (IgG) play a central role in cellular immune defenses. Three types of such receptors have been identified: A 72 kilodalton (D) receptor with high affinity for monomeric IgG is found on monocytes and some macrophages, a 40 D receptor with low affinity for monomeric IgG is found on monocytes, neutrophils, eosinophils, platelets, and certain human tumor-cell lines, and a 50–70 D receptor with low affinity for monomeric IgG is found on neutrophils, eosinophils, natural killer cells, and macrophages. These three types of Fcγ receptor are referred to as FcγRI, FcγRII, and FcγRIII, respectively: Unkeless et al., Ann. Rev. Immunol., Vol. 6, pgs. 251–281 (1988).

It is believed that FcγRIII-mediated removal of IgG-coated platelets plays an important part in the pathogenesis of immune thrombocytopenic purpura (ITP), a platelet-deficiency condition characterized by excessive bleeding: von dem Borne, pgs. 222–256, in Immunohaematology, Engelfriet et al., eds. (Elsevier, Amsterdam, 1984). Clerkson et al., New England J. Med., Vol. 314,pgs. 1236–1239 (1986) , report that the infusion of ligand-blocking anti-FcγRIII antibody into a patient with refractory ITP resulted in transient increase in platelet count. This observation suggests that the most deleterious manifestation of ITP could be temporarily ameliroated by the administration of agents that block or compete with FcγRIII for binding sites on IgG-coated platelets.

In a separate area of clinical immunology, elevated serum levels of aggregates consisting of immunoglobulin and antigen (so-called "immune complexes") have been correlated with a wide variety of disorders, particularly autoimmune diseases, such as systemic lupus erythematosus (SLE), and rheumatoid arthritis. The level of such complexes has become an important diagnostic for presence of autoimmune disorder; e.g. Theofilopoulos et al., Am.J. Pathol., Col. 100, pgs. 531–591 (1980).

Present assays for the serum level of immune complexes include solid-phase assays which take advantage of the affinity of the complexes for certain complement or rheumatoid factor proteins, and cellular assays which take advantage of the property of Raji cells to preferentially bind immune complexes; Theofilopoulos et al., chapter 28, and Toth et al., chapter 29, in Rose et al., eds. Manual of Clinical Immunology, 3rd Ed. (American Society for Microbiology, Washington, D.C., 1986). Unfortunately, like many mammalian-cell based assays, the Raji-cell assay is difficult to perform, and requires elaborate controls and standards because of the inherent variability of Raji-cell binding to immune complexes.

In light of the foregoing, it would be advantageous for the medical community to have alternative assay methods for immune complexes utilizing well characterized, widely available, and conveniently cultured cell lines. It would also be advantageous if soluble FcγRs could be produced in sufficient quantity to permit practical emergency therapy for refractory cases of ITP.

SUMMARY OF THE INVENTION

The present invention is directed to soluble and membrane-bound human FcγRIII polypeptides, their muteins, nucleic acids capable of encoding the same, and diagnostic and therapeutic uses of such polypeptides and muteins.

Figure 1B:
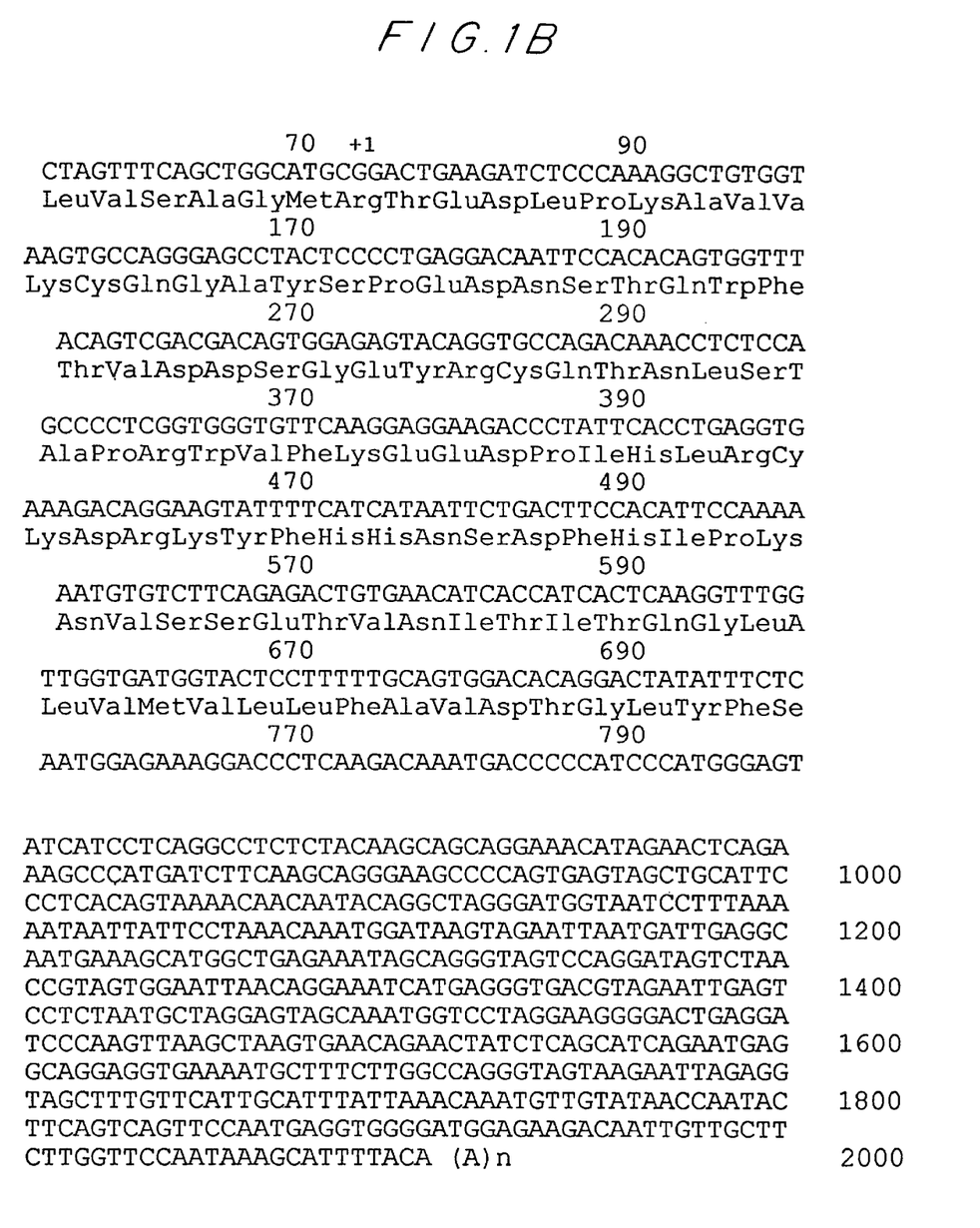

The invention is based on the discovery of a cDNA encoding a human FcγRIII. A cDNA clone, pcD(SRα) containing the FcγRIII-encoding insert (illustrated in FIG. 1) is deposited in E. coli K12 strain MC1061 with the American Type Culture Collection (ATCC), Rockville, Md. USA, under accession number 67707.

The invention therefore provides a protein consisting of soluble or membrane-bound human FcγRIII and having the the amino acid sequence:

Arg - Thr - Glu - Asp - Leu - Pro - Lys - Ala -

Val - Val - Phe - Leu - Glu - Pro - Gln - Trp -

Tyr - Arg - Val - Leu - Glu - Lys - Asp - Ser -

Val - Thr - Leu - Lys - Cys - Gln - Gly - Ala -

Tyr - Ser - Pro - Glu - Asp - Asn - Ser - Thr -

Gln - Trp - Phe - His - Asn - Glu - Asn - Leu -

Ile - Ser - Ser - Gln - Ala - Ser - Ser - Tyr -

Phe - Ile - Asp - Ala - Ala - Thr - Val - Asp -

Asp - Ser - Gly - Glu - Tyr - Arg - Cys - Gln -

Thr - Asn - Leu - Ser - Thr - Leu - Ser - Asp -

Pro - Val - Gln - Leu - Glu - Val - His - Val -

Gly - Trp - Leu - Leu - Leu - Gln - Ala - Pro -

Arg - Trp - Val - Phe - Lys - Glu - Glu - Asp -

Pro - Ile - His - Leu - Arg - Cys - His - Ser -

Trp - Lys - Asn - Thr - Ala - Leu - His - Lys -

Val - Thr - Tyr - Leu - Gln - Asn - Gly - Lys -

Asp - Arg - Lys - Tyr - Phe - His - His - Asn -

-continued

Ser - Asp - Phe - His - Ile - Pro - Lys - Ala -

Thr - Leu - Lys - Asp - Ser - Gly - Ser - Tyr -

Phe - Cys - Arg - Gly - Leu - Val - Gly - Ser -

Lys - Asn - Val - Ser - Ser - Glu - Thr - Val -

Asn - Ile - Thr - Ile - Ser - Ser - Phe - Ser -

Pro - Pro - Gly

Formula I or

Arg - Thr - Glu - Asp - Leu - Pro - Lys - Ala -

Val - Val - Phe - Leu - Glu - Pro - Gln - Trp -

Tyr - Arg - Val - Leu - Glu - Lys - Asp - Ser -

Val - Thr - Leu - Lys - Cys - Gln - Gly - Ala -

Tyr - Ser - Pro - Glu - Asp - Asn - Ser - Thr -

Gln - Trp - Phe - His - Asn - Glu - Asn - Leu -

Ile - Ser - Ser - Gln - Ala - Ser - Ser - Tyr -

Phe - Ile - Asp - Ala - Ala - Thr - Val - Asp -

Asp - Ser - Gly - Glu - Tyr - Arg - Cys - Gln -

Thr - Asn - Leu - Ser - Thr - Leu - Ser - Asp -

Pro - Val - Gln - Leu - Glu - Val - His - Val -

Gly - Trp - Leu - Leu - Leu - Gln - Ala - Pro -

Arg - Trp - Val - Phe - Lys - Glu - Glu - Asp -

Pro - Ile - His - Leu - Arg - Cys - His - Ser -

Trp - Lys - Asn - Thr - Ala - Leu - His - Lys -

Val - Thr - Tyr - Leu - Gln - Asn - Gly - Lys -

Asp - Arg - Lys - Tyr - Phe - His - His - Asn -

Ser - Asp - Phe - His - Ile - Pro - Lys - Ala -

Thr - Leu - Lys - Asp - Ser - Gly - Ser - Tyr -

Phe - Cys - Arg - Gly - Leu - Val - Gly - Ser -

Lys - Asn - Val - Ser - Ser - Glu - Thr - Val -

Asn - Ile - Thr - Ile - Ser - Ser - Phe - Phe -

Pro - Pro - Gly;

Formula II together with variant proteins wherein one amino acid residue is deleted, and 0–2 amino acid residues, other than Cys, Phe, Trp and Tr, are replaced according to the following substitution Table:

| Amino Acid | Can be replaced by |
|---|---|
| Ala | Ser, Thr or Gly |
| Arg | Lys |
| Asn | Asp or Ser |
| Asp | Glu or Asn |
| Gln | Glu |
| Glu | Asp or Gln |
| Gly | Ala or Ser |
| His | Asn |
| Ile | Val or Leu |
| Leu | Val or Ile |
| Lys | Arg or Asn |
| Met | Leu |
| Pro | Ala |
| Ser | Ala, Thr, Gly or Asn |
| Thr | Ser, Ala or Lys |
| Val | Ile, Ala or Leu. |

For the variant proteins, this substitution Table presents the group of additional L-amino acids that are synonymous to the amino acids that can be replaced. Synonymous amino acids within a group have sufficiently similar physiochemical properties for substitution between members of the group to preserve the biological function of the molecule, Grantham, *Science*, Vol. 185, pgs. 862–864 (1974); and Dayhoff et al., *Atlas of Protein Sequence and Structure* 1972, Vol. 5, pgs. 89–99.

Furthermore, it is clear that deletions of amino acids may also be made in the above-identified sequences without altering biological function, particularly if only one amino acid is acid is deleted and amino acids that are critical to a functional conformation are not removed or displaced, e.g. some cysteine residues: Anfinsen, "Principles That Govern The Folding of Protein Chains", *Science*, Vol. 181, pgs. 223–230 (1973). Proteins and muteins produced by deletions are within the purview of the present invention. Whenever an amino acid residue of a protein of Formula I or II is referred to herein by number, such a number is in reference to the N-terminus of the protein.

In particular, 1–2 amino acid residues (especially 1) other than Arg, Gln, His, Met and Pro, can be replaced according to the following substitution Table:

| Amino Acid | Can be replaced by |
|---|---|
| Ala | Ser |
| Asn | Asp |
| Asp | Glu |
| Glu | Asp |
| Gly | Ala |
| Ile | Val |
| Leu | Val |
| Lys | Arg |
| Ser | Ala or Thr |
| Thr | Ser or Ala |
| Val | Ile. |

As used herein, "N-fold substituted" in reference to Formula I or II describes a group of amino acid sequences differing from the native amino acid sequences thereof by zero-N substitutions, such that the replacing amino acid is selected from the appropriate group of amino acids synonymous the amino acid at the location of the substitution. That is, if the amino acid residue Ala is at the location for substitution, then that Ala can be replaced with Ser, Thr or Gly.

Likewise, as used herein, the term "N-fold deleted" in reference to Formula I or II describes a group of amino acid sequences differing from the native amino acid sequences thereof by zero-N deletions of amino acids.

Throughout, standard abbreviations are used to designate amino acids, nucleotides, restriction endonucleases, and the like; e.g. Cohn, "Nomenclature and Symbolism of α-Amino Acids," *Methods in Enzymology*, Vol. 106, pgs. 3–17 (1984); Wood et al. *Biochemistry: A Problems Approach*, 2nd ed. (Benjamin, Menlo Park, 1981); and Roberts, "Directory of Restriction Endonucleases", *Methods in Enzymology*, Vol. 68, pgs. 27–40 (1979).

A particularly preferred feature of the present invention is that part of the protein that consists of the extracellular domain of a human FcγRIII.

BRIEF DESCRIPTION OF THE DRAWINGS

FIGS. 1A & 1B (on two sheets to be read side-by-side) illustrates the nucleotide sequence of the cDNA insert of pcD(SRα)-GP5;

FIGS. 3A & 3B (on two sheets to be read side-by-side) illustrate the nucleotide sequence of the cDNA insert of pcD(SRα)-NL10.

DETAILED DESCRIPTION OF THE INVENTION

The present invention includes nucleic acids encoding polypeptides capable of binding to the Fc portion of human IgG. These polypeptides are derived from human FcγRIII. The invention includes soluble and membrane-bound polypeptides for human FcγRIII. These and other modified versions of the polypeptides are readily produced using standard protein engineering techniques.

Once nucleic acid sequence and/or amino acid sequence information is available for a native protein, a variety of techniques become available for producing virtually any mutation in the native sequence. Shortle, in *Science*, Vol. 229, pgs 1193–1201 (1985), reviews techniques for mutating nucleic acids which are applicable to the present invention. Preferably, mutants of the protein of the present invention are produced by site-specific oligonucleotide-directed mutagenesis, e.g. Zoller and Smith, *Methods in Enzymology*, Vol. 100, pgs. 468–500 (1983), and Mark et al., U.S. Pat. No. 4,518,584 entitled "Human Recombinant Interleukin-2 Muteins", which are incorporated by reference; or by so-called "cassette" mutagenesis described by Wells et al. in *Gene*, Vol. 34, pgs. 315–323 (1985), by Estell et al. in *Science*, Vol. 233, pgs. 659–663 (1986), and also essentially by Mullenbach et al. in *J. Biol. Chem.*, Vol. 261, pgs. 719–722 (1986), and by Feretti et al. in *Proc. Natl. Acad. Sci.*, Vol. 83, pgs. 597–603 (1986).

Polypeptides with amino acid modifications (i.e. muteins) may be desirable in a variety of circumstances. For example, undesirable side effects might be reduced by certain muteins, particularly if the side effect is associated with a different part of the polypeptide from that of the desired activity. In some expression systems, the native polypeptide may be susceptible to degradation by proteases. In such cases, selected substitutions and/or deletions of amino acids which change the susceptible sequences can significantly enhance yields, e.g. British patent application 2173-804-A where Arg at position 275 of human tissue plasminogen activator is replaced by Gly or Glu. Muteins may also increase yields in purification procedures and/or increase shelf lives of proteins by eliminating amino acids susceptible to oxidation, acylation, alkylation, or other chemical modifications. For example, methinoine readily undergoes oxidation to form a sulfoxide, which in many proteins is associated with loss of biological activity: e.g. Brot and Weissbach, *Arch. Biochem. Biophys.*, Vol. 223, pg. 271 (1983). Methionines can often be replaced by more inert amino acids with little or no loss of biological activity, e.g. Australian patent application AU-A-52451/86. In bacterial expression systems, yields can sometimes be increased by eliminating or replacing conformationally inessential cysteine residues, e.g. Mark et al., U.S. Pat. No. 4,518,584.

Preferably, soluble forms of the FcγRIII of the invention are produced by introducing a stop codon prior to (i.e. in the 5'- or "upstream" direction of) the coding region for the transmembrane and intracellular portion of the FcγRIII cDNA. This is conveniently done by site-specific mutagenesis. Transmembrane regions are readily identified by the presence of an amino acid segment containing from about 20–25 residues having high average hydrophobicity, e.g. Wickner, *Science*, Vol. 210, pgs. 861–868 (1980), and Greene et al., *Ann. Rev. Immunol.*, Vol. 4, pgs. 69–95 (1986).

Plasmid pcD(SRα)-GP5 is similar to the pcD shuttle vector described by Okayama and Berg, *Mol. Cell. Biol.*, Vol. 2, pgs. 161–170 (1983), and Vol. 3, pg 280–289 (1983), except that the SV40 promoter has been modified to improve expression by the downstream insertion of a portion of the long terminal repeat (LTR) from a HTLV(I) retrovirus, described by Takebe et al., *Mol. Cell. Biol.*, Vol. 8, pgs. 466–472 (1988). The plasmid is conveniently propagated in *E. coli* K12 strain MC1061, or like host.

The immunoglobulin G binding property of the FcγRIIIs of the invention is measured by standard techniques, e.g. (1) in the case of membrane-bound FcγRIII: the ability of cells transfected with the FcγRIII cDNA to form rosettes in the presence of IgG-coated red blood cells (RBCs) or to preferentially bind human IgG aggregated by heat treatment; or (2) in the case of soluble FcγRIII: the ability to preferentially remove FcγRIII from solution by an immunoadsorbent column comprising human IgG, or to inhibit rosette formation between IgG-coated RBCs and cells known to have FcγRIIIs. The former measurements can be made with fluorescently labeled human IgG molecules, e.g. Haugland, *Handbook of Fluorescent Probes* (Molecular Probes, Inc., Junction city, Oreg. 1985). The latter measurements can be made by constructing an IgG column from isolated human IgG and a commercially available activated sepharose column, e.g. from Bio-Red Laboratories (Richmond, Calif.).

Rosette assays are standard in the art, e.g. Winchester et al., chapter 31, in Rose et al., eds., *Manual of Clinical Laboratory Immunology*, 3rd Ed. (American Society for Microbiology, Washington, D.C., 1986).

Once the cDNA of the invention has been cloned, a wide range of expression systems (i.e. combinations of host and expression vector) can be used to produce the proteins of the invention. Possible types of host cells include, but are not limited to, bacterial, yeast, insect, mammalian, and the like. Selecting an expression system, and optimizing protein production thereby, involves the consideration and balancing of many factors, including (1) the nature of the protein to be expressed, e.g. the protein may be posionous to some host organisms, it may be susceptible to degradation by host proteases, or it may be expressed in inactive conformations or in insoluble form in some hosts, (2) the nature of the messenger RNA (mRNA) corresponding to the protein of interest, e.g. the mRNA may have sequences particularly susceptible to host endonucleases, which drastically reduce the functional lifetime of the mRNA, or the mRNA may form secondary structures that mask the start codon or ribosome binding site, thereby inhibiting initiation of translation in some hosts (3) the selection, availability, and arrangement of host-compatible exprssion-control sequences in the 3'- and 5'-regions flanking the coding region—these include promoters, 5'- and 3'-protector sequences, ribosome binding sites, trancription terminators, enchancers, polyadenylate addition sites, cap sites, intron-splice sites, and the like, (4) whether the protein has a secretion-signal sequence which can be processed by the host, or whether an expression-control sequence encoding a signal sequence endogenous to the host must be spliced onto the region encoding the mature protein, (5) the available modes and efficiencies of transfection or transformation of the host, and whether transient or stable expression is desired, (6) the scale and cost of the host culture system desired for expressing the protein, (7) whether, and what type of, posttranslational modifications are desired, e.g. the extent and kind of glycosylation desired may affect the choice of host, (8) the ease with which the expressed protein can be separated from proteins and other materials of the host cells and/or culture medium e.g. in some cases it may be desirable to express a fusion protein with a specialized signal sequence to aid in later purification steps, e.g. Sassenfeld et al., *Biotechnology*, January 1984, (9) the stability and copy number of a particular vector in a selected host, e.g. Hofschneider et al., eds. *Gene Cloning in Organisms Other than E. coli* (Springer Verlag, Berlin, 1982), and (10) like factors known to those skilled in the art.

Many reviews are available which provide guidance for making choices and/or modifications of specific expression systems in light of the recited factors, e.g.de Boer and Shepard, "Strategies for Optimizing Foreign Gene Expression in *Escherichia coli*" pgs. 205–247, in Kroon, ed. *Genes: Structure and Expression* (John Wiley & Sons, New York, 1983), review serval *E. coli* expression systems; Kucherlapati et al., *Critical Reviews in Biochemistry*, Vol. 16, Issue 4, pgs. 349–379 (1984), and Benerji et al., *Genetic Engineering*, Vol. 5, pgs. 19–31 (1983), review methods for transfecting and transforming mammalian cells; Reznikoff and Gold, eds., *Maximizing Gene Expression* (Butterworths, Boston, 1986) review selected topics in gene expression in *E. coli*, yeast, and mammalian cells; and Thilly, *Mammalian Cell Technology* (Butterworths, Boston, 1986) reviews mammalian expression systems.

Likewise, many reviews are available which describe techniques and conditions for linking and/or manipulating specific cDNAs and expression control sequences to create and/or modify expression vectors suitable for use with the present invention: e.g. Maniatis et al., *Molecular Cloning: A Laboratory Manual* (Cold Spring Harbor Laboratory, N.Y., 1982); Glover, *DNA Cloning: A Practical Approach*, Vol. I and II (IRL Press, Oxford, 1985) and Perbal, *A Practical Guide to Molecular Cloning* (John Wiley & Sons, N.Y., 1984).

Suitable expression systems for the invention include those disclosed by Itakura and Riggs, U.S. Pat. No. 4,704,362 (bacterial expression), by Clerk et al., U.S. Pat. No. 4,675,285 and by Hamer U.S. Pat. No. 4,599,308 (mammalian expression), and by Kurjan et al., U.S. Pat. No. 4,546,082 (yeast expression). Accordingly, the above patents are incorporated by reference.

Whenever SV40-based vectors are used, e.g. pcD vectors, a preferred host is the cos7 cell line, decribed by Gluzman, *Cell*, Vol. 23, pgs. 175–182 (1981) and available from the ATCC under accession number CRL1651.

Soluble FcγRIIIs of the invention are administered as a pharmaceutical composition for treating ITP. Such compositions contain an effective amount of the FcγRIII in a pharmaceutical carrier. A pharmaceutical carrier can be any compatible, non-toxic substance suitable for delivering the compositions of the invention to a patient. Generally, compositions useful for parenteral administration of such drugs are well Known, e.g. *Remington's Pharmaceutical Science*, 15th Ed. (Mack Publishing Company, Easton, Pa. 1980). Alternatively, compositions of the invention may be introduced into a patient's body by an implantable drug delivery system, e.g. Urguhart et al., *Ann. Rev. Pharmacol. Toxicol.*, Vol. 24, pgs. 199–236 (1984).

When administered parenterally, the soluble FcγRIIIs will be formulated in a unit dosage injectable form (solution, suspension, emulsion) in association with a pharmaceutical carrier. Such carriers are inherently non-toxic and non-therapeutic. Examples of such carriers are normal saline, Ringer's solution, dextrose solution, and Hank's solution. Nonaqueous carriers such as fixed oils and ethyl oleate may also be used. A preferred carrier is 5% dextrose/saline. The carrier may contain minor amounts of additives such as substances that enhance isotonicity and chemical stability, e.g., buffers and preservatives. The soluble FcγRIII is preferably formulated in purified form substantially free of aggregates and other proteins at a concentration in the range of about 5 to 30 mg/ml, and preferably at a concentration in the range of about 10 to 20 mg/ml.

Selecting an administration regimen to deliver to a patient an amount of soluble FcγRIII which is effective in ameliorating the thrombopenia associated with ITP depends on several factors, including the serum turnover rate of the soluble FcγRIII, the serum level of competing endogenous FcγRIII associated with the immune disorder, the possible immunogenicity of the soluble FcγRIII, and the like. Preferably, an administration regimen maximizes the amount of soluble FcγRIII delivered to the patient consistent with an acceptable level of side effects. Accordingly, the amount of soluble FcγRIII delivered depends in part on the particular soluble FcγRIII employed and the severity of the disease being treated. Guidance in selecting appropriate doses is found in the literature on therapeutic uses of antibodies and antibody fragments, which are polypeptides of roughly the same size as the soluble FcγRIIIs, e.g. Bach et al., chapter 22, in Ferrone et al., eds., *Handbook of Monoclonal Antibodies* (Noges Publications, Park Ridge, N.J., 1985); and Russell, pgs. 303–357, and Smith el al., pgs. 365–389, in Haber et al., eds. *Antibodies in Human Diagnosis and Therapy* (Raven Press, New York., 1977). Preferably, the dose is in the range of about 1–20 mg/kg per day, more preferably about 1–10 mg/kg per day.

EXAMPLES

The following examples serve to illustrate the present invention. Selection of vectors and hosts as well as the concentration of reagents, temperatures, and the values of other variables are only to exemplify application of the present invention and are not to be considered limitations thereof.

Example I

Construction of Stable Mammalian Cell Transformants Which Express Human FcγRIII

Preferably, mammalian cell lines capable of stable expression of the FcγRIII are produced by cotransfecting a host mamalian cell with a vector carrying a selectable marker and a vector carrying a host-compatible promoter and the FcγRIII cDNA insert. For pcD(SRα)-GP5, suitable hosts include Chinese hamster ovary cells, COS monkey cells, and mouse L cells, such as a thymidine kinase deficient mutant (tk$^-$) L cell available from the American Type Culture Collection under accession number CCL 1.3. The selectable marker allows one to select host cells which have a high probability of containing the FcγRIII gene fully integrated into the host genome. Typically, the ratio of pcD(SRα)-GP5 to the marker-containing vector in the transfection solution is about 10:1. Thus, if the marker gene is integrated into the host genome, it is very likely that pcD(SRα)-GP5 will also be integrated by virtue of its higher concentration. The selectable marker also provides a means of preventing the cultures of desired transformants from being overgrown by revertant cells.

tk$^-$ mouse L cells are cotransfected with pcD(SRα)-GP5 and pSV2tk, a pSV2 plasmid carrying a thymidine kinase gene under control of the SV40 early promoter. The pSV2 plasmid is described by Mulligan et al., *Science*, Vol. 209, pgs. 1422–1427 (1980), and by Subramani et al., *Mol. Cell. Biol.*, Vol. 1, pgs. 854–864 (1981), and is available from the American Type Culture Collection under accession number 37146. Both plasmids are amplidied in *E. coli*, e.g. strain HB101 available from the ATCC under accession number 33694, and purified by cesium chloride equilibrium centrifugation. A suspension of abut 1×10$^5$ of tk$^-$ L cells in 10 ml of Dulbecco's Modified Eagle Medium (DME) with 10% fetal bovin serum is placed in a Falcon 3003 dish and cultured at 37° C. for 20 hours in a 5% carbon dioxide gas incubator, after which the medium is replaced by 10 ml of fresh DME with 10% fetal bovine serum. The culture is incubated for an additional 4 hours. After incubation, 0.5 ml of solution (50 mM Hepes, 280 mM NaCl, 1.5 mM sodium phosphate buffer, pH 7.22) and 0.5 ml of solution B (2M CaCl$_2$, 10 μg pcD(SRα)-GP5, 1 μg pSV2tk) are added to the culture medium, and the culture is incubated at 37° C. for 24 hours in a 5% CO$_2$ atmosphere, after which the cells are placed in a selective medium with HAT (e.g. Sigma Chemical Co., St. Louis, Mo.). After two weeks the surviving colonies are subcloned by limiting dilution, and clones are assayed for expression of FcγRIII.

Example II

Use of Stable L Cell Transformant Expressing Membrane-bound FcγRIII to Measure Serum Levels of Immune Complex A stably transformed mamalian cell expressing the FCγRIII of the invention can replace the Raji cell line in assays for immune complexes, e.g. Theofilopoulos et al., chapter 28, *Manual of Clinical Laboratory Immunology*, 3rd Ed. (American Society for Microbiology, Washington, D.C. 1986).

Antiserum to human IgG is prepared in rabbits, and the IgG fraction is isolated by ammonium sulfate precipitation followed by fractionation on an anion-exchange chromatography column (DEAE-cellulose 52; Whatman Chemical Separation Ltd., Maidstone, England). Antiserum from commercial sources may also be used. The IgG fraction of the antiserum is brought to 5 mg/ml, and 1 ml is labeled with $^{125}$I. After iodination and dialysis, the antiserum is diluted to 1 mg/ml with phosphate-buffered saline (PBS) to give a specific activity of about 3×10$^5$ cpm/μg. Cells transformed with the FcγRIII cDNA are harvested after 72 hours of culture, and portions of 2×10$^6$ cells in 200 μl of medium are placed in 1.5-ml plastic Eppendorf conical tubes (Brinkmann Instruments, Inc., Westbury, N.Y., catalog no. 22-36-411-1). One ml. of Spinner medium (Eagle minimal medium without Ca$^{2+}$ and Mg$^{2+}$) is added to each tube, and the cells are centrifuged at 800×g for 8 min. Supernatant fluids are aspirated, and the cell pellets are resuspended in 50 μl of Spinner medium. Serum to be tested is diluted fourfold in 0.05 M NaCl (physiological saline), and 25 μl is added to the transformed cells. After a 45-min incubation period at 37° C. with gentle shaking by hand every 5 to 10 min, the cells are washed three times with Spinner medium. After the final wash, the cells, gently shaken every 5 to 10 minutes, are allowed to react for 30 min at 4° C. with $^{125}$I-labeled rabbit anti-human IgG diluted with Spinner medium containing 10 g of human serum albumin (HSA) per liter. After incubation, the cells are washed three times, supernatant fluids are completely aspirated, and radioactivity of the cell pellet is determined in a gamma counter. All assays are done in duplicate. The amount of uptake, expressed as absolute counts, percentage of the input, or micrograms of antibody, is referred to a standard curve of radioactive antibody uptake by cells incubated with normal human serum (complement source) containing various amounts of aggregated human IgG (AHG). The quantity of immune complex in serum is equated to an amount of AHG after correction for the dilution factor and is expressed as micrograms of AHG equivalent per milliliter of serum. The soluble AHG is formed from a solution of 6.5 mg of Cohn fraction II or isolated human IgG per ml of physiological saline, heated at 63° C. for 30 min, and centrifuged (1,500×g, 15 min) to remove insoluble large aggregated. The supernatant is then diluted with buffer to yield a final concentration of approximately 1.6 mg/ml. Portions (0.5 ml) of this preparation are stored at −70° C. and can be used for as long as 1 month.

The standard curve of radioactive antibody uptake is constructed as follows. Fifty-microliter portions of AHG (80 μg of protein) are serially diluted (11 twofold dilutions) in saline. Subsequently, 50 μl of a twofold dilution of normal human serum (source of complement), freshly obtained or stored at −70° C., is added to each dilution of AHG, mixed carefully, and incubated at 37° C. for 30 min. Thereafter, 25 μl of each mixture is added to 2×10$^6$ cells in duplicate (fourfold final dilutions of serum containing form 20 μg to about 20 ng of AHG); the mixture is incubated, washed, and reacted with radiolabeled antibody. Radioactivity is then counted as with the test sera. A base line of radioactive antibody uptake (background) by cells incubated with 25 μl of a fourfold dilution of normal human serum, used as a source of complement in the reference curve, is also established.

Standard preparatins of IgG aggregates and of tetanus toxoid-human anti-tetanus toxoid immune complexes have recently been developed under the auspices of the International Union of Immunologists and are available through the Swiss Red Cross Blood Transfusion Service, e.g. Nydegger et al., *Clin. Exp. Immunol.*, Vol. 58, pgs. 502–509 (1984).

Example III

Construction of a Soluble Human FcγRIII

Soluble RcγRIII was constructed using site-specific oligonucleotide-directed mutagenesis of the FcγRIII cDNA insert of pcD(SRα)-GP5. The entire cDNA insert of pcD (SRα)-GP5 was subcloned as a 2.4 kilobase Bam HI fragment into the Bluescript KS plasmid (Stratagene, San Diego, Calif.) and single-stranded DNA was then prepared.

Figure 2:
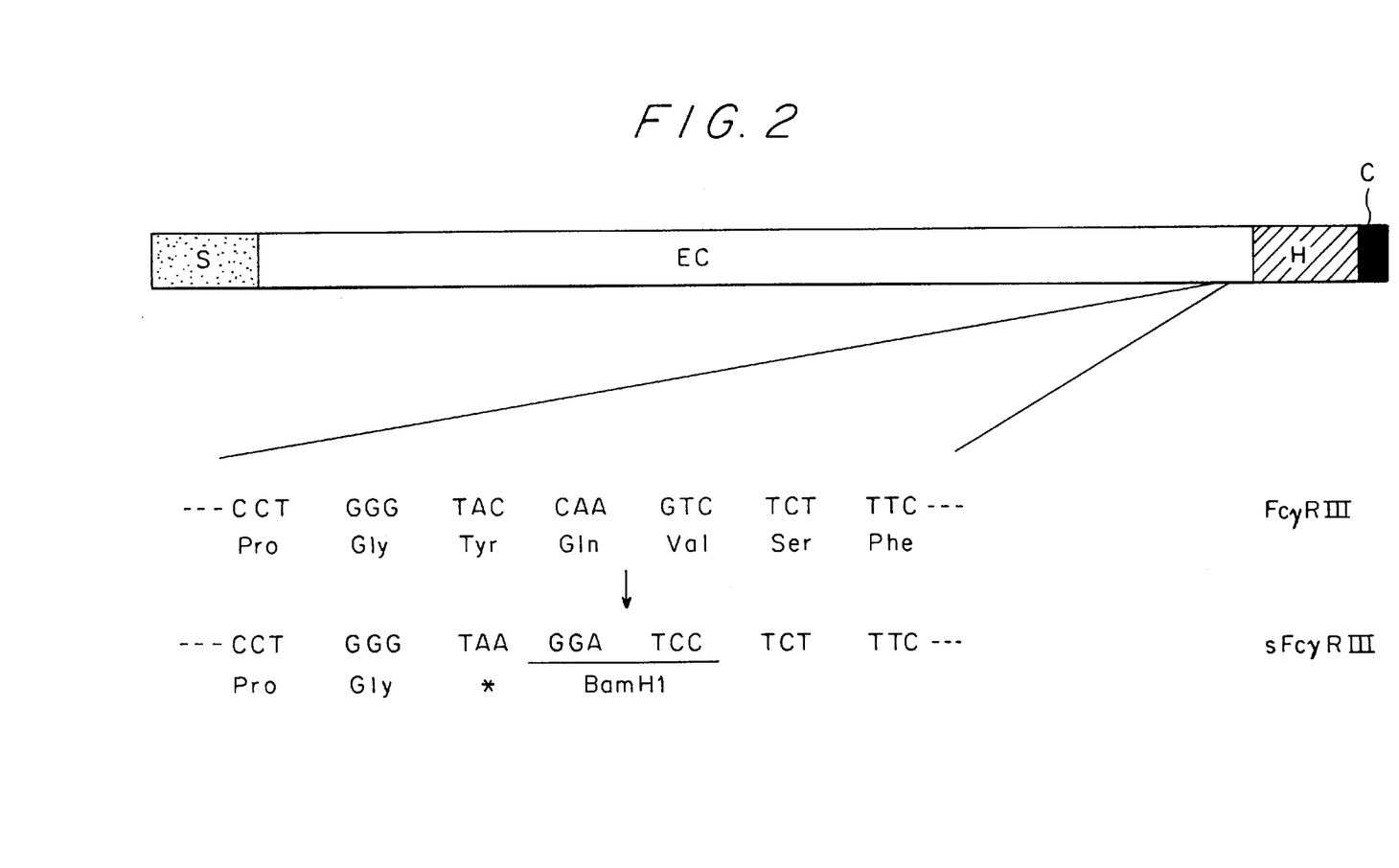
FIG. 2 illustrate the relative location of the stop codon inserted to produce a soluble human FcγRIII, secreted as an FCγRIII mutant.

A synthetic oligonucleotide (minimum size about 18 nucleotides) encoding a TAA stop codon and a Bam HI site (with mutations shown in boldface in FIG. 2) was used as primer for complementary strand synthesis using DNA polymerase I large fragment (Amersham, Arlington Heights, Ill.). FIG. 2 indicates the position of the stop codon and Bam HI site relative to the major domains encoded by the FcγRIII cDNA: S represents the region encoding the signal peptide, EC represents the region encoding the extracellular domain of FcγRIII, H represents the region encoding the hydrophobic, or transmembrane, domain of FcγRIII, and C represents the region encoding the cytoplasmic domain. Introducing the stop codon as indicated by FIG. 2 produces a mutant FcγRIII lacking both the cytoplasmic and transmembrane domains; it is soluble as shown by the designation "sFcγRIII" beside the modified DNA sequence. After the identity of the mutant was confirmed by DNA sequence analysis, it was subocloned back into the Bam HI site of the pcD(SRα) vector, amplified in E coli, and transfected into COS 7 cells by electroporation. One day prior to transfection, approximately $(1.5–2.0) \times 10^6$ COS 7 monkey cells were seeded onto individual 100 mm plates in Dulbecco's modified Eagle's medium (DME) containing 6% fetal calf serum and 2 mM glutamine. To perform the transfection, cells were harvested by trypsinization and counted, washed twice in serum-free DME, and suspended to $(1–7) \times 10^6$ cells per ml in serum-free DME. DNA was added to 25 µg/ml and the mixture was allowed to stand at room temperature for 10 minutes, after which 0.8 ml was pulsed in a 0.4 cm sterile cuvette with a Bio Rad (Richmond, Calif.) Gene pulser at 250 volts and 960 microfarads. After pulsing, cells were allowed to stand for 10 minutes and then were plated at $(1.54–2.0) \times 10^6$ per 100 mm plate in DME plus 6% fetal calf serum. Superantants were harvested and assayed for soluble FcγRIII after 72 hours.

The soluble FcγRIII in the COS7 culture supernatants was analyzed further by gel electrophoresis, and immunoprecipitated. A control, Experiment 1, and six actual experiments, Experiments 2 to 7, were performed. Experiments 1, 3 and 6 and each contained proteins from culture supernatants of COS7 cells transfected with the pcD carrying the soluble FcγRIII cDNA. Proteins from Experiment 1 were immunoprecipitated with a non-specific mouse $IgG_2$ antibody; proteins form Experiment 3 were immunoprecipitated with human IgG, presumably by the binding of the Fc portion of the antibody with the soluble FcγRIII; and proteins from Experiment 6 were immunopreciptated with the monoclonal antibody 3G8 which is specific for the extracellular domain of FcγRIII. The soluble FcγRIII corresponded to a broad band at about 40 kilodaltons. Experiment 4 and 7 contained proteins from culture supernatants of COS7 cells transfected with the pcD carrying the soluble FcγRIII cDNA and cultured in the presence of tunicamycin. Tunicamycin inhibits the post-translational attachment of N-linked carbohydrates to proteins. It was applied in an attempt to determine the nature of the apparent heterogeneity of the 40 kilodalton band. The tunicamycin caused the appearance of two bands of lower molecular weight, which is consistent with the deglycosylation of the soluble FcγRIII. Tunicamycin was added to the cultures as disclosed by Martens et al., PNAS 84: 809–813 (1987). Experiments 2 and 5 contained proteins from culture supernatants of COS7 cells which had undergone the same manipulations as the COS cells of Experiments 3 and 4 and Experiments 6 and 7, respectively, with the exception the no plasmid DNA was included in the transfection protocol.

Example IV

Isolation of a Variant Human FcγRIII from Natural Killer Cells

Figure 3B:
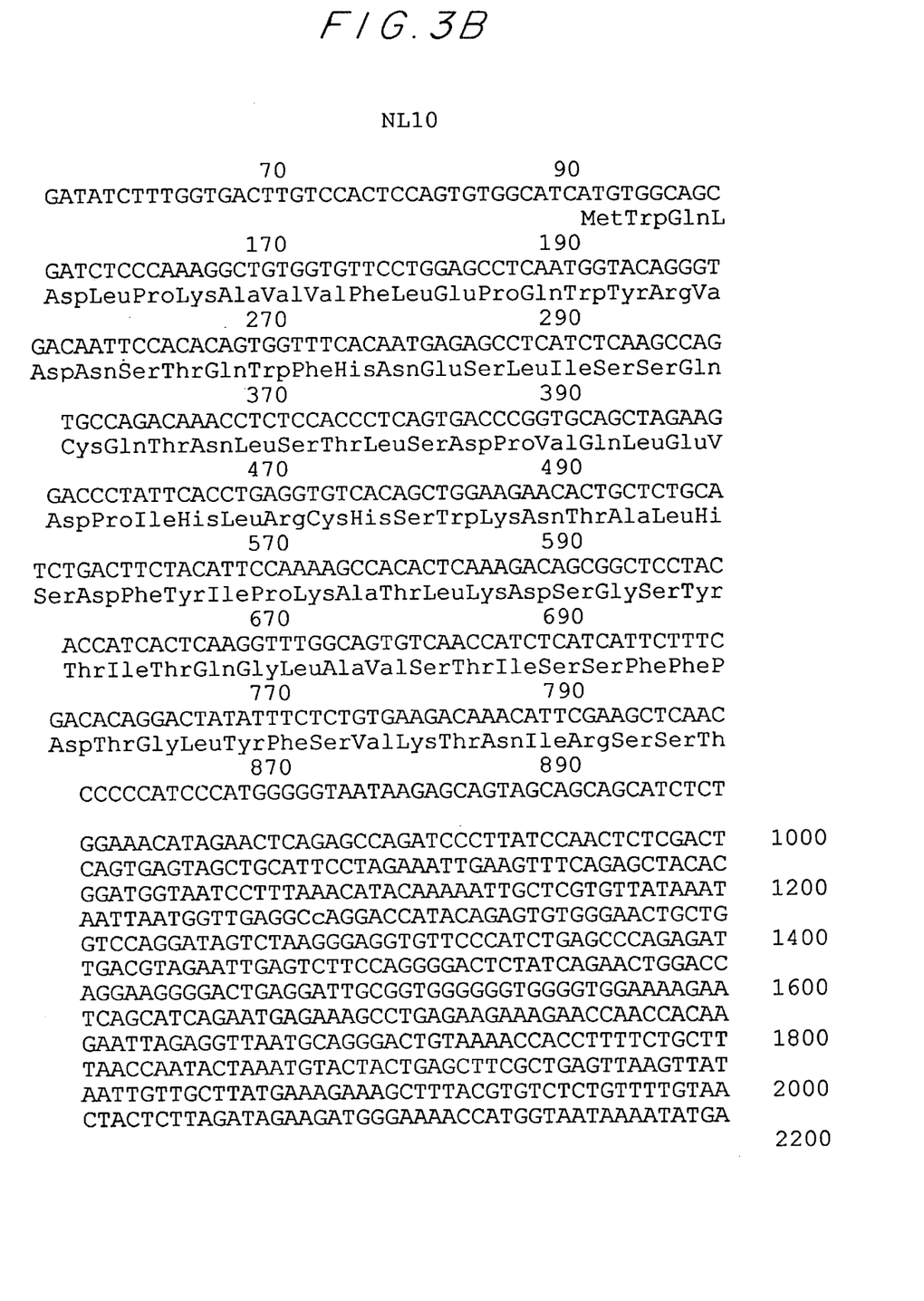

A cDNA library was constructed from mRNA extracted from a human natural killer (NK) cell line using the pcD (SRα) expression vector. The library was screened with a probe constructed from the cDNA insert of pcD(SRα)-GP5, which was radiolabeled with $^{31}$by random-primed DNA labeling (Boehringer Mannheim, Indianapolis, Ind.). A clone pcD(SRα)-NL10 was obtained that exhibited human IgG binding activity. The sequence of the cDNA insert of pcD (SRα)-NL10 is illustrated in FIGS. 3A & 3B. It can be seen that the amino acid sequence of the FcγRIII and that encoded by pcD(SRα)-GP5 are very similar, differing in the extracellular domain by only six amino acids.

The descriptions of the foregoing embodiments of the invention have been presented for purpose of illustration and description. They are not intended to be exhaustive or to limit the invention to the precise forms disclosed, and obviously many modifications and variations are possible in light of the above teaching. The embodiments are chosen and described in order to best explain the principles of the invention and its practical application to thereby enable others skilled in the art to best utilize the invention in various embodiments and with such modifications as are suited to the particular use contemplated. It is intended that the scope of the invention be defined by the claims appended hereto.

Applicants have deposited pcD(SRα)-GP5 with the American Type Culture Collection Rockville, Md., USA (ATCC), under accession number 67707. This deposit is made under the Budapest Treaty for the Deposit of Microorganisms; and also under conditions as provided under ATCC's agreement for Culture Deposit for Patent purposes, which assures that the deposit will be made available to the US Commissioner of Patents and Trademarks pursuant to 35 U.S.C. 122 and 37 C.F.R. 1.14, and will be made available to the public upon issue of a U.S. patent, which requires that the deposit be maintained. Availability of the deposited strain is not to be construed as a license to practice the invention in contravention of the rights granted under the authority of any government in accordance with its patent laws.

What is claimed is:

1. A method for detecting immune complexes in a sample, comprising the steps of:

providing host cells transformed with a vector carrying a cDNA insert encoding a FcγRIII molecule, wherein the FcγRIII molecule is expressed on the surface of the transformed host cells and is expressed form the group consisting of the following sequences:

Arg-Thr-Glu-Asp-Leu-Pro-Lys-Ala-Val-Val-Phe-Leu-

Glu-Pro-Gln-Trp-Tyr-Arg-Val-Leu-Glu-Lys-Asp-Ser-

Val-thr-Leu-Lys-Cys-Gln-gly-Ala-Tyr-Ser-Pro-Glu-

Asp-Asn-Ser-Thr-Gln-Trp-Phe-his-Asn-Glu-Asn-Leu-

Ile-Ser-Ser-Gln-Ala-Ser-Ser-Tyr-Phe-Ile-Asp-Ala-

Ala-Thr-Val-Asp-Asp-Ser-Gly-Glu-tyr-Arg-Cys-Gln-

Thr-Asn-Leu-Ser-Thr-Leu-Ser-Asp-Pro-Val-Gln-Leu-

Glu-Val-his-Val-Gly-Trp-Leu-Leu-Leu-Gln-Ala-Pro-

Arg-Trp-Val-Phe-Lys-Glu-Glu-Asp-Pro-Ile-His-Leu-

Arg-Cys-His-Ser-Trp-Lys-Asn-Thr-Ala-Leu-His-Lys-

Val-Thr-Tyr-Leu-Gln-Asn-Gly-Lys-Asp-Arg-lys-Tyr-

Phe-His-His-Asn-Ser-Asp-Phe-His-Ile-Pro-Lys-Ala-

-continued

Thr-Leu-Lys-Asp-Ser-Gly-Ser-Tyr-Phe-Cys-Arg-Gly-

Leu-Val-Gly-Ser-Lys-Asn-Val-Ser-Ser-Glu-Thr-Val-

Asn-Ile-Thr-Ile-Thr-gln-Gly-Leu-Ala-Val-Ser-Thr-

Ile-Ser-Ser-Phe-Ser-Pro-Pro-Gly;

and

Arg-Thr-Glu-Asp-Leu-Pro-Lys-Ala-Val-Val-Phe-Leu-

Glu-Pro-Gln-Trp-Tyr-Arg-Val-Leu-glu-Lys-Asp-Ser-

Val-thr-Leu-Lys-Cys-Gln-gly-Ala-Tyr-Ser-Pro-Glu-

Asp-Asn-Ser-Thr-gln-Trp-Phe-His-Asn-Glu-Ser-Leu-

Ile-Ser-Ser-Gln-Ala-Ser-Ser-Tyr-Phe-Ile-Asp-Ala-

Ala-Thr-VAl-Asp-Asp-Ser-Gly-Glu-Tyr-Arg-Cys-Gln-

Thr-Asn-Leu-Ser-Thr-Leu-Ser-Asp-Pro-Val-Gln-Leu-

Glu-Val-His-Ile-Gly-Trp-Leu-Leu-Leu-Gln-Ala-Pro-

Arg-Trp-Val-Phe-Lys-glu-Glu-Asp-Pro-Ile-his-Leu-

Arg-Cys-His-Ser-Trp-Lys-Asn-thr-Ala-Leu-His-Lys-

-continued

Val-Thr-Tyr-Leu-gln-Asn-Gly-Lys-Gly-Arg-Lys-Tyr-

Phe-His-His-Asn-Ser-Asp-Phe-tyr-Ile-Pro-Lys-Ala-

Thr-Leu-Lys-Asp-Ser-Gly-Ser-Tyr-Phe-Cys-Arg-Gly-

Leu-Phe-Gly-Ser-Lys-Asn-Val-Ser-Ser-glu-Thr-Val-

Asn-Ile-Thr-Ile-Thr-Gln-Gly-Leu-Ala-Val-Ser-Thr-

Ile-Ser-Ser-Phe-Phe-Pro-Pro-Gly;

exposing the transformed host cells to a sample so that any immune complex present in the sample adheres to FcγRIII molecules expressed on the surface of the transformed host cells; labeling any immune complex adhering to FcγRIII molecules on the surfaces of the transformed host cells; and measuring the amount of labeled immune complex adhering to the transformed host cells.

2. The method according to claim 1, wherein the transformed host cells are selected from the group consisting of mouse L cells and COS monkey cells and the vector is selected from the group consisting of pcD(SRα)-GP5 and pcD(SRα)-NL10.

* * * * *